United States Patent
Saeki et al.

[11] Patent Number: 5,105,016
[45] Date of Patent: Apr. 14, 1992

[54] BIS(CYCLOHEXYLPHENOL) COMPOUNDS AND THEIR USE

[75] Inventors: Kazumi Saeki, Nakatsu; Akira Shimada, Moriguchi, both of Japan

[73] Assignee: Yoshitomi Pharmaceutical Industries, Ltd., Osaka, Japan

[21] Appl. No.: 613,748

[22] PCT Filed: Mar. 20, 1990

[86] PCT No.: PCT/JP90/00382
§ 371 Date: Nov. 20, 1990
§ 102(e) Date: Nov. 20, 1990

[87] PCT Pub. No.: WO90/11274
PCT Pub. Date: Apr. 10, 1990

[30] Foreign Application Priority Data
Mar. 25, 1989 [JP] Japan .................................. 1-73456

[51] Int. Cl.$^5$ ............................................ C07C 317/14
[52] U.S. Cl. .................................................... 568/33
[58] Field of Search ......................... 568/33, 34; 585/3

[56] References Cited
U.S. PATENT DOCUMENTS

| | | | |
|---|---|---|---|
| 3,252,911 | 5/1966 | Orloff | 585/3 |
| 3,345,328 | 10/1967 | Tholstrup | 260/45.85 |
| 3,449,441 | 6/1969 | Dewhurst | 260/609 |
| 3,676,530 | 7/1972 | Robin et al. | 568/33 |
| 4,287,366 | 9/1981 | Yamaguchi et al. | 568/33 |

FOREIGN PATENT DOCUMENTS
64-20228 1/1989 Japan .
64-29422 1/1989 Japan .

*Primary Examiner*—Marianne Cintins
*Assistant Examiner*—Margaret Argo
*Attorney, Agent, or Firm*—Wenderoth, Lind & Ponack

[57] ABSTRACT

Bis(cyclohexylphenol) compounds of the formula

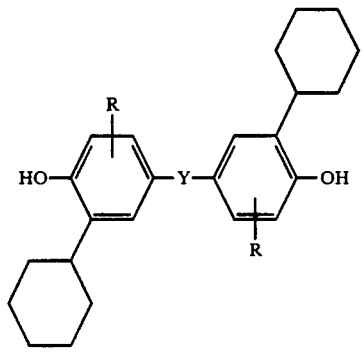

wherein R is an alkyl having 1 to 6 carbon atoms, Y is —S—, —SO— or —SO$_2$— with the proviso that when R is methyl in the ortho position to the hydroxy, Y is —SO— or —SO$_2$—and their use. The above-mentioned compounds are useful as antioxidants and biocides for industrial use.

1 Claim, No Drawings

BIS(CYCLOHEXYLPHENOL) COMPOUNDS AND THEIR USE

TECHNICAL FIELD

The present invention relates to bis(cyclohexylphenol) compounds which are novel and useful as antioxidants or biocides for industrial use, and to their use.

BACKGROUND ART

It has been disclosed in AU 532353 that bisphenolsulfone compounds of the formula

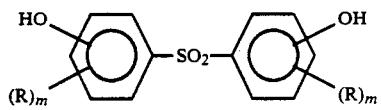

wherein R is hydrogen, halogen, alkyl, cycloalkyl, aryl, aralkyl, hydroxy, alkoxy, aryloxy, carboxyl or carboalkoxy, m is an integer of 1 to 3, and when m is not less than 2, the groups represented by R may be the same or different and two of them, when adjacent to each other, may combinedly form a benzene ring, can be obtained by oxidation of the corresponding sulfoxide compounds or sulfone compounds using hydrogen peroxide in the presence of an alkali, and that said compounds are useful as light stabilizers, polyolefin modifiers, lubricants, additives, agrochemicals, and intermediates thereof. Further, it is described in Chemical Abstracts, 76, 25, 153267m that 4,4'-thiobis(6-cyclohexyl-2-methylphenol) is useful as a nonstaining stabilizer for polymers.

The above-mentioned Australian patent discloses 4,4'-diphenolsulfone, 4,4'-bis(2-tert-butyl-5-methylphenol)sulfone, 4,4'-bis(2-phenylphenol)sulfone, etc. as examples of 4,4'-bisphenolsulfone compounds, whereas no specific description can be found about alkyl-substituted cyclohexylphenol compounds. In addition, previously known 4,4'-thiobis(2-methyl-6-cyclohexylphenol) poses a problem that it colors polymers in actual use. It has not been known that these compounds exhibit biocidal action on wood destroying fungi.

DISCLOSURE OF THE INVENTION

The present inventors conducted intensive studies for the purpose of providing compounds useful as antioxidants or biocides for industrial use and found that certain bis(cyclohexylphenol) compounds show excellent action, which resulted in completion of the invention. Thus, the present invention relates to bis(cyclohexylphenol) compounds of the formula

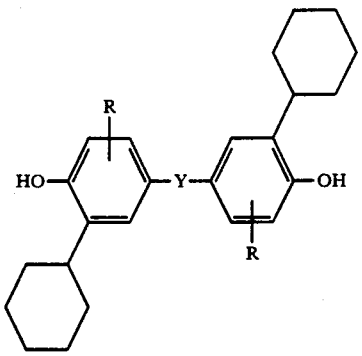

wherein R is an alkyl having 1 to 6 carbon atoms, Y is —S—, —SO— or —SO$_2$— with the proviso that when R is methyl in the ortho position to the hydroxy, Y is —SO— or —SO$_2$— [hereinafter referred to as compounds (I)] and to their use.

In the above definition, the alkyl having 1 to 6 carbon atoms is, for example, methyl, ethyl, propyl, isopropyl, butyl, isobutyl, tert-butyl, pentyl, isopentyl, neopentyl, hexyl, etc.

The preferred compounds (I) are compounds wherein R is alkyl having 1 to 6 carbon atoms and Y is —SO$_2$—. Particularly preferred are 4,4'-sulfonylbis(6-cyclohexyl-3-methylphenol) and 4,4'-sulfonylbis(6-cyclohexyl-2-methylphenol).

The compounds (I) of the present invention can be produced, for example, by the following methods.

(1) When Y is a sulfur atom:

A compound of the formula

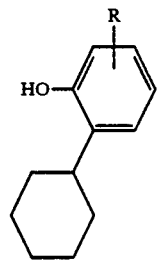

wherein R is as defined above, is reacted with a sulfur compound, such as sulfur, sulfur monochloride or sulfur dichloride.

The reaction normally proceeds in a suitable solvent (e.g. methylene chloride, dichloroethane, chloroform, carbon tetrachloride, tetrachloroethane, acetic acid, carbon disulfide, acetonitrile, hexane, heptane, ligroin, petroleum benzine, etc.) in the presence of an acidic catalyst (e.g. sulfuric acid, boron trifluoride, tin tetrachloride, aluminum chloride, zinc chloride, trifluoroacetate, pyridine hydrochloride, pyridine sulfuric anhydride complex, iron chloride, etc.) at −20° to 150° C., preferably about 0° to 40° C. The acidic catalyst is used in a proportion of about 0.01 to 10 moles per mole of the compound of formula (II).

(2) When Y is sulfinyl or sulfonyl:

The compounds (I) of the present invention can be produced by subjecting the compound wherein Y is a sulfur atom, which is produced by the method (1) mentioned above, to oxidation reaction. The oxidizing agents for the oxidation are exemplified by, but not limited to, peroxides such as hydrogen peroxide, peracetic acid, perbenzoic acid and so on, and inorganic oxidizing agents such as calcium permanganate, potassium periodate, and so on.

The reaction normally proceeds in a solvent inert to the reaction (a polar solvent such as acetone, methanol or acetic acid is preferred) at about −20° to 120° C., preferably at about 0° to 100° C. When the oxidation is conducted in moderate conditions, the corresponding sulfinyl compound is obtained.

The compounds (I) thus obtained can be purified by a conventional means such as column chromatography, recrystallization and so on.

The compounds (I) of the present invention exhibit superior action in that they do not color resins (e.g. polyethylene, etc) and improve heat stability of resins, and thus, they are useful as antioxidants for industrial use. In addition, they show excellent biocidal action on wood destroying fungi such as *Tyromyces palustris, Coriolus versicolor* and so on, and are useful as biocides for industrial use.

When the compounds of the present invention are used as antioxidants for industrial use, they may be contained in a proportion of 0.01 to 1.0% relative to resin, and may be used further in combination with known antioxidants and light stabilizers.

When the compounds of the present invention are used as biocides, they can be formulated into powders, wettable powders, suspensions, etc. by mixing with carriers, diluents, surfactants, dispersing agents, pigments, etc. The compounds of the present invention are preferably contained in an amount of 0.1-50% by weight.

As biocides, the compounds of the present invention can be used singly or in combination. It is also possible to use the compounds of the present invention combinedly with known biocide compounds.

Hereinbelow, the present invention is described in detail by working examples. The compounds obtained were identified by infrared absorption spectrometry, nuclear magnetic resonance spectrometry, mass spectrometry, elemental analysis, etc.

EXAMPLE 1

Production of 4,4'-thiobis(6-cyclohexyl-3-methylphenol)

To a solution of 3-methyl-6-cyclohexylphenol (9.5 g), acetonitrile (25 ml) and anhydrous zinc chloride (0.05 g) is added sulfur dichloride (3 g) in acetonitrile (5 ml). After 3 hours' stirring at the same temperature, the mixture is kept standing overnight at room temperature. The acetonitrile is distilled off under reduced pressure, and the residue is dissolved in toluene (200 ml). After thorough washing with water, the toluene is distilled off under reduced pressure. The residue is subjected to silica gel column chromatography, and eluted with a mixture of toluene and ethyl acetate (9:1). The solvent is distilled off from the single peak eluate fraction (identified by thin-layer chromatography), and the residue is recrystallized from n-heptane to give 4,4'-thiobis(6-cyclohexyl-3-methylphenol) as colorless needles, m.p. 128°–130° C.

EXAMPLE 2

Production of 4,4'-sulfinylbis(6-cyclohexyl-3-methylphenol)

To a solution of crude oily 4,4'-thiobis(6-cyclohexyl-3-methylphenol) (10.5 g) in methanol (40 ml) is gradually added dropwise 30% hydrogen peroxide (6.5 g) at room temperature. The mixture is stirred for a while at the same temperature, and left standing at 50° C. for 3 hours and overnight at room temperature. The precipitated crystals are filtered off, washed with cool methanol and dried to give 4,4'-sulfinylbis(6-cyclohexyl-3-methylphenol), m.p. 151°–153° C.

EXAMPLE 3

Production of 4,4'-sulfonylbis(6-cyclohexyl-3-methylphenol)

The semi-solid oily 4,4'-thiobis(6-cyclohexyl-3-methylphenol) is dissolved in acetic acid (100 ml), to which 35% hydrogen peroxide (9.7 g) is added at 40° C. over a period of 2 hours. Further, 35% hydrogen peroxide (20 g) is added thereto at 50°–60° C. over a period of 6 hours. After the reaction, water is added thereto and the water layer is decanted off. Dichloroethane is added to the resulting oily substance to allow precipitation. The crystals are filtered off and recrystallized from ethanol to give 4,4'-sulfonylbis(6-cyclohexyl-3-methylphenol), m.p. 301° C. (decomposition).

EXAMPLE 4

Production of 4,4'-sulfonylbis(6-cyclohexyl-2-methylphenol)

To a solution of 2-methyl-6-cyclohexylphenol (8.5 g) in acetonitrile (40 ml) is added sulfur dichloride (2.8 g) in acetonitrile (10 ml) at 15° C. The mixture is stirred at the same temperature for 8 hours, and the acetonitrile is distilled off. The residue is dissolved in toluene (150 ml), washed thoroughly with water, and the toluene is distilled off. The residue thus obtained is subjected to silica gel column chromatography and eluted with toluene. From the single peak eluate fraction (identified by thin-layer chromatography) is obtained 4,4'-thiobis(2-methyl-6-cyclohexylphenol).

The oily 4,4'-thiobis(6-cyclohexyl-2-methylphenol) (4.3 g) obtained above is dissolved in acetic acid (40 ml), and thereto is added 30% hydrogen peroxide (5.9 g) at 40° C. over a period of 1 hour, followed by stirring at 65°–70° C. for 5 hours. The mixture is cooled, and the precipitated crystals are filtered off and recrystallized from a mixture of ethanol and toluene to give 4,4'-sulfonylbis(6-cyclohexyl-2-methylphenol), m.p. 264°–265° C.

In the same manner, there can be obtained the following compounds.
4,4'-sulfinylbis(6-cyclohexyl-2-methylphenol)
4,4'-thiobis(6-cyclohexyl-3-ethylphenol)
4,4'-thiobis(3-tert-butyl-6-cyclohexylphenol)
4,4'-sulfinylbis(3-tert-butyl-6-cyclohexylphenol)
4,4'-sulfonylbis(3-tert-butyl-6-cyclohexylphenol)
4,4'-sulfonylbis(2-tert-butyl-6-cyclohexylphenol)

The present invention has been fully explained in the description and examples given above, but any variations and modifications thereof may be made without departing from the spirit and scope of the present invention.

We claim:
1. 4,4'-Sulfonylbis(6-cyclohexyl-3-methylphenol).

* * * * *